United States Patent [19]

Stocking et al.

[11] Patent Number: 5,704,914

[45] Date of Patent: Jan. 6, 1998

[54] CATHETER PLACEMENT ASSEMBLY

[76] Inventors: John E. Stocking, 9905 Winged Foot Dr., Louisville, Ky. 40223; Francis Duque, 3807 Washington Sq., Louisville, Ky. 40207

[21] Appl. No.: 605,926

[22] Filed: Feb. 23, 1996

[51] Int. Cl.$^6$ ................................ A61M 5/178
[52] U.S. Cl. .................. 604/164; 604/167; 604/168; 604/195
[58] Field of Search ................ 604/164, 167, 604/168, 195

[56] References Cited

U.S. PATENT DOCUMENTS

| | | | |
|---|---|---|---|
| 3,995,628 | 12/1976 | Gula et al. | 128/214.4 |
| 4,068,659 | 1/1978 | Moorehead | 128/214.4 |
| 4,205,675 | 6/1980 | Vaillancourt | 128/214.4 |
| 4,230,123 | 10/1980 | Hawkins, Jr. | 128/658 |
| 4,274,408 | 6/1981 | Nimrod | 128/214.4 |
| 4,306,562 | 12/1981 | Osborne | 128/348 |
| 4,417,886 | 11/1983 | Frankhouser et al. | 604/53 |
| 4,447,235 | 5/1984 | Clarke | 604/169 |
| 4,464,171 | 8/1984 | Garwin | 604/53 |
| 4,493,707 | 1/1985 | Ishihara | 604/164 |
| 4,515,592 | 5/1985 | Frankhouser | 604/163 |
| 4,525,157 | 6/1985 | Vaillancourt | 604/52 |
| 4,834,718 | 5/1989 | McDonald | 604/195 |
| 4,842,591 | 6/1989 | Luther | 604/283 |
| 4,850,961 | 7/1989 | Wanderer et al. | 604/53 |
| 4,894,052 | 1/1990 | Crawford | 604/53 |
| 4,961,729 | 10/1990 | Vaillancourt | 604/164 |
| 5,013,304 | 5/1991 | Russell et al. | 604/167 |
| 5,246,426 | 9/1993 | Lewis et al. | 604/168 |
| 5,261,895 | 11/1993 | Kablik | 604/249 |
| 5,269,771 | 12/1993 | Thomas et al. | 604/213 |
| 5,295,970 | 3/1994 | Clinton et al. | 604/168 |
| 5,308,336 | 5/1994 | Hart et al. | 604/167 |
| 5,324,270 | 6/1994 | Kayan et al. | 604/157 |
| 5,356,390 | 10/1994 | Erskine | 604/164 |
| 5,356,394 | 10/1994 | Farley et al. | 604/256 |
| 5,385,554 | 1/1995 | Brimhall | 604/168 |
| 5,409,464 | 4/1995 | Villalobos | 604/167 |

Primary Examiner—Sam Rimell
Assistant Examiner—Luke Yeh
Attorney, Agent, or Firm—Maurice L. Miller, Jr.

[57] ABSTRACT

A catheter assembly is disclosed which includes a flexible catheter, a hub attached to the catheter which defines a lumen and an adjoining flash back chamber which communicate with the catheter, and a flexible resilient diaphragm attached to the hub through which a hypodermic needle such as a catheter introducer needle can be passed. The diaphragm prevents a liquid, such as blood, which has been introduced into the hub lumen from flowing past the diaphragm and beyond the hub when the diaphragm is unpenetrated. A hollow tubular body may also be included to which a cannulated catheter needle can be either stationarily or movably attached. The body is removably attached to the hub behind the diaphragm. If movably attached to the body, the needle has a retracted position fully recessed within the body for safe storage and an advanced operative position extending through the diaphragm, hub and catheter. A needle occluding member may also be provided to prevent a liquid such as blood from flowing through the needle into the body. The member may be a movable guide wire or a stationary obturator member. A liquid outlet port can be provided on the side of the hub and a multi-position stop cock can be mounted on the hub to direct liquid flow from the catheter to the side port while blocking flow toward the diaphragm and vise versa.

39 Claims, 6 Drawing Sheets

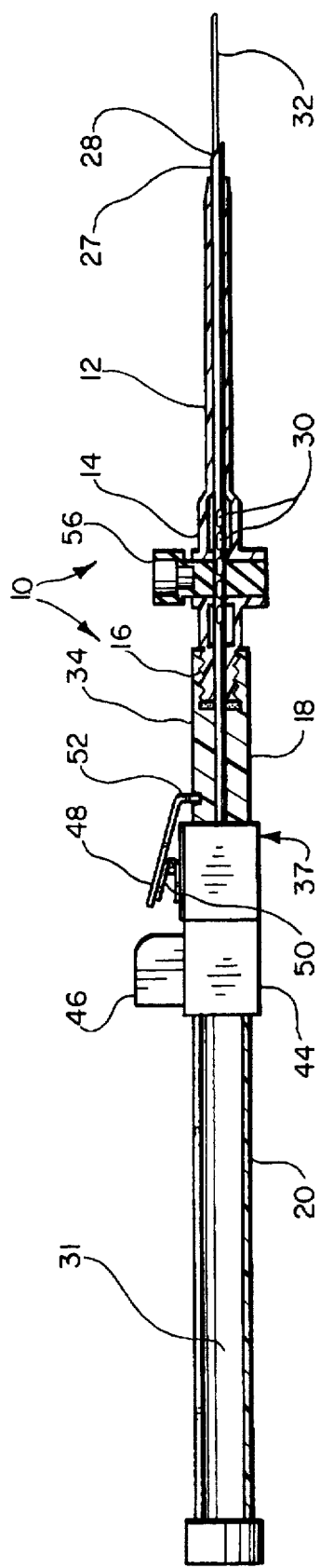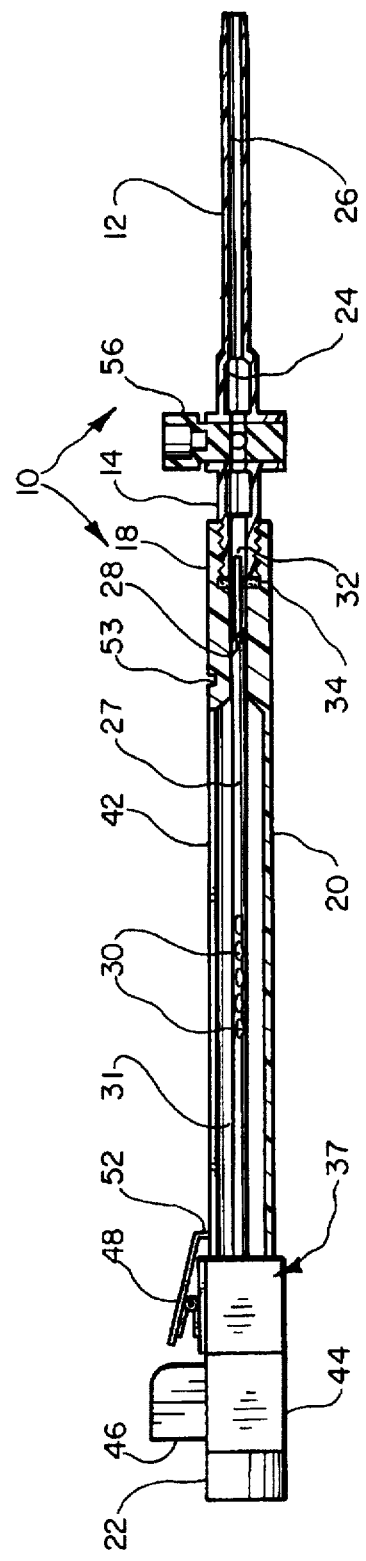
FIG. 3
FIG. 4

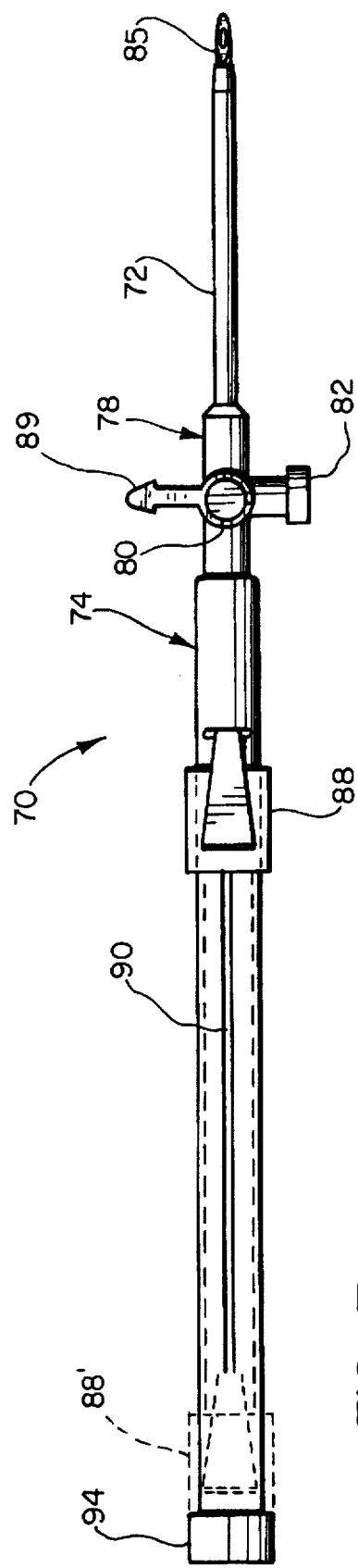
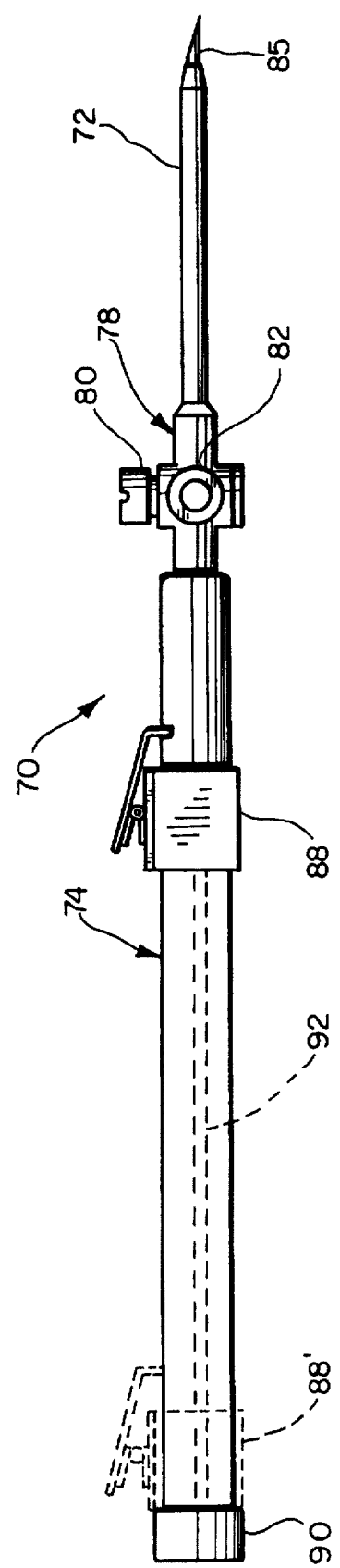
FIG. 7
FIG. 8

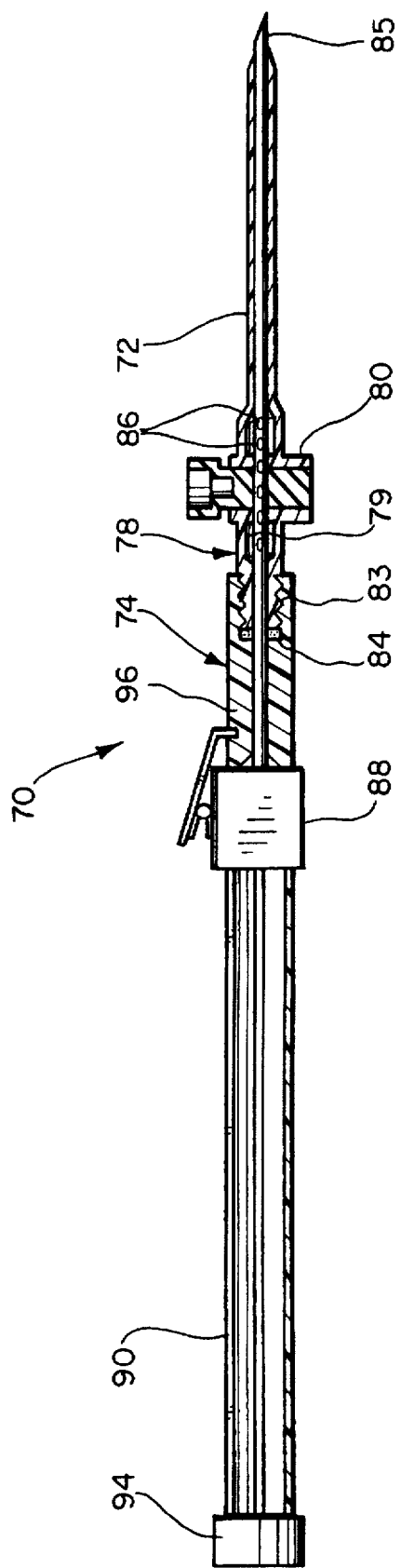
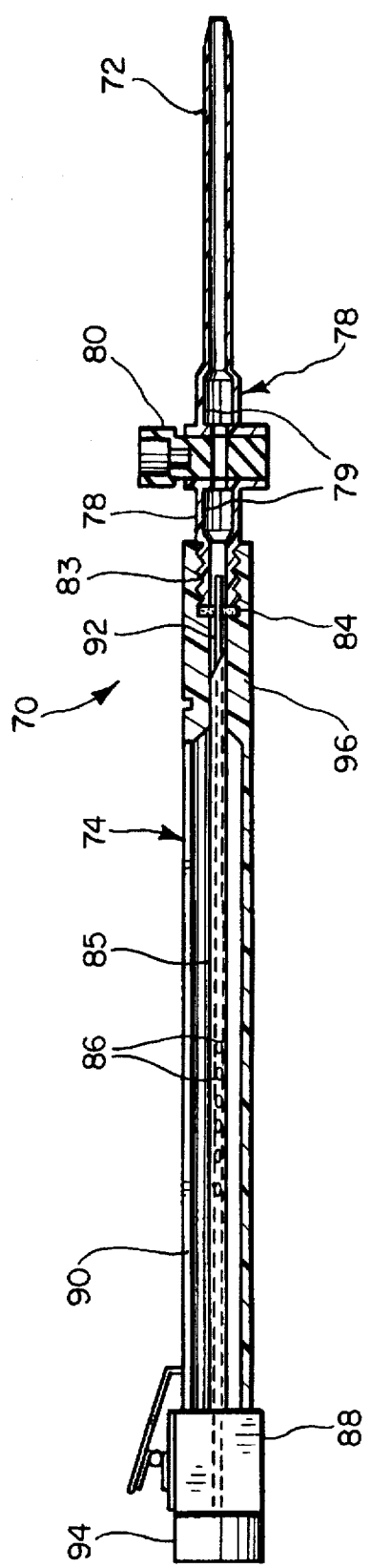
FIG. 9
FIG. 10

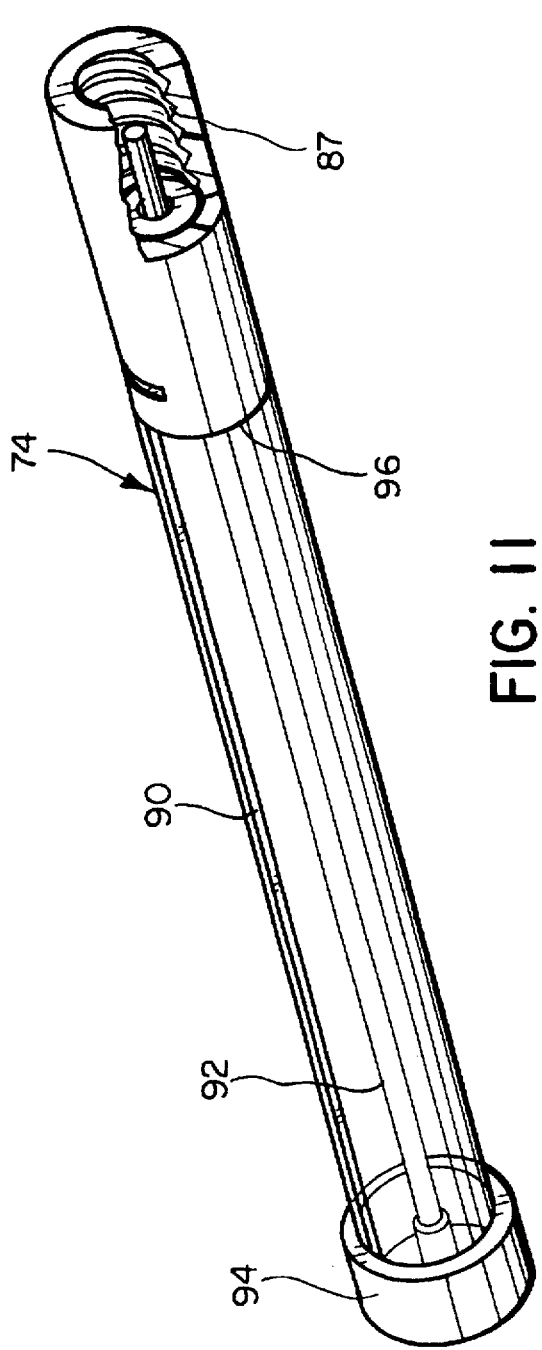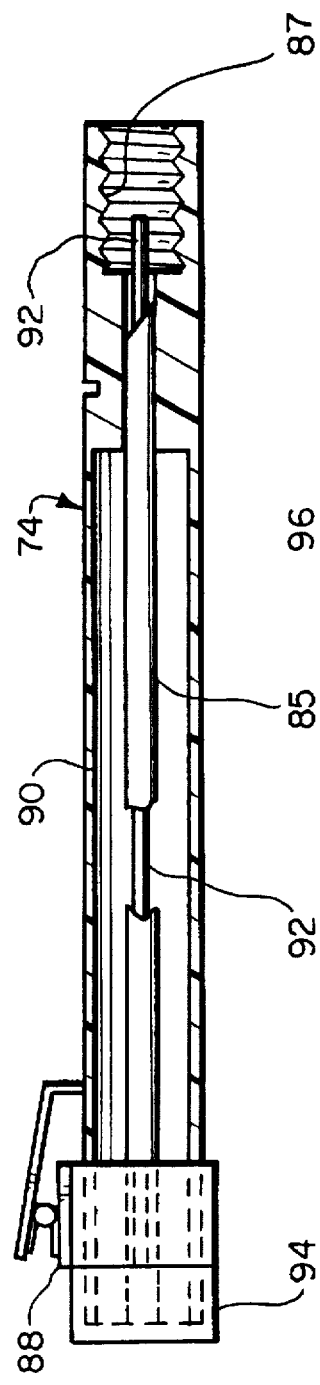

CATHETER PLACEMENT ASSEMBLY

FIELD OF THE INVENTION

This invention relates generally to catheter assemblies of the type through which a catheter introducer needle is passed in close fitting relationship in order to place a catheter into a liquid containing region, such as a blood vessel, of a biological organism. More specifically, this invention relates to means for preventing the spillage of a biological liquid, such as blood, from such assemblies during and after use and for providing visual indications of blood flash back.

BACKGROUND OF THE INVENTION

Broadly speaking, devices for the introduction of a catheter into a blood vessel or other liquid containing region of a patient have long been known and used in the prior art. See, for example, U.S. Pat. No. 5,356,390 issued to T. J. Erskine on Oct. 18, 1994; U.S. Pat. No. 4,417,886 issued to P. L. Frankhouser on Nov. 29, 1983; U.S. Pat. No. 4,205,675 issued to V. L. Vaillancourt on Jun. 3, 1980; U.S. Pat. No. 4,068,659 issued to H. R. Moorehead on Jan. 17, 1978; U.S. Pat. No. 3,995,628 issued to J. A. Gula, et al. on Dec. 7, 1976; U.S. Pat. No. 4,447,235 issued to J. M. Clarke on May 8, 1984; and U.S. Pat. No. 5,246,426 issued to J. P. Lewis et al. on Sep. 21, 1993.

The Frankhouser device contains a catheter and a cannulated catheter introducer needle. The needle is permanently mounted in fixed relationship in a clear plastic hub. A hollow guide wire robe, containing a guide wire when the wire is in a retracted position, is friction fitted into the end of the needle hub so that the guide wire is aligned for entry into a cannula of the needle. The guide wire is fastened in a collar slidably located in the hollow interior of the guide wire tube. A handle is attached to the slidable collar and extends through a longitudinally extending slot on the tube to permit the guide wire to be manually inserted through the needle cannula and into and along a blood vessel lumen of a patient to form a track along which to guide the catheter. Thereafter, the guide wire is retracted from the blood vessel along the needle cannula back into the guide wire tube. The needle hub, with the guide wire tube attached, is then disconnected from a hub of the catheter to allow access to the blood vessel of the patient through the catheter hub as needed.

One problem encountered using this type of prior art catheter placement assembly is that the stationarily mounted needle is exposed when removed from the catheter hub and is thus capable of causing a dangerous needle stick during handling by medical personnel and others prior to and during disposal of the unit. Another problem is that blood can leak from the needle cannula into the hollow interior of the guide wire tube both before the guide wire is advanced from the guide wire tube into the needle cannula and after the guide wire is withdrawn from the needle cannula back into the tube. Such blood can then leak through the elongated slot along which the guide wire handle is moved to become a source of contamination. Yet another problem encountered is blood leaking or flowing freely through an open proximal end of the catheter hub after the guide wire tube has been disconnected from the hub. Moreover, after obtaining an initial blood flash back to show proper needle placement using this prior art type of assembly, resulting in blood being introduced into the wire guide tube, advancement of the guide wire will necessarily result in blood spillage from the guide wire tube as the handle moves distally along the handle slot. Indeed, subsequent retraction of the guide wire to confirm proper needle placement or to reposition the needle to achieve proper needle placement will also necessarily result in blood spillage through the handle slot of the wire guide tube.

By means of our invention, these and other difficulties encountered using prior art catheter assemblies are substantially overcome.

SUMMARY OF THE INVENTION

It is an object our invention to provide a novel catheter assembly.

It is another object of our invention to provide a catheter assembly having means for preventing the spillage of biological fluids, such as blood, therefrom during and following use.

It is yet another object of our invention to provide a novel catheter assembly which includes a fenestrated catheter introducer needle movable between a retracted storage position recessed in a hollow tube safe from causing an accidental needle stick following use and an advanced operative position.

It is a further object of our invention to provide a catheter assembly which includes a transparent or translucent hub attached to the catheter for observing blood flash back in a lumen thereof and which also includes a side access port attached to the hub which communicates with the hub lumen.

It is still a further object of our invention to provide a catheter assembly having multiple ports for accessing a catheter which includes a liquid flow switching means for switching the catheter between different access ports as desired.

Briefly, in accordance with our invention, there is provided a catheter assembly including a flexible catheter defining a passageway therethrough and a hub having a distal end attached to a proximal end of the catheter. The hub contains a lumen therethrough which communicates with the catheter passageway. A liquid sealing means is also included through which a hypodermic needle, such as a catheter introducer needle can be passed. The sealing means is attached to the hub for preventing a liquid which has been introduced into the hub lumen from flowing through the sealing means. A needle attachment body is also included which is removably connected to the hub. A cannulated catheter introducer needle is also included which contains a sharp tip on a free end thereof and which has an opposite end attached to the body such that the needle has at least one position relative to the body which is operative to project through the sealing means, hub lumen and catheter passageway when the body is attached to the hub for introducing the catheter into a liquid containing region of a biological organism. The needle contains at least one fenestration on a central portion thereof which communicates with a cannula of the needle and with the hub lumen and which is positioned distally of the sealing means when the needle is disposed in its operative position.

These and other objects, features and advantages of the present invention will become apparent to those skilled in the art from a study of the following detailed description and attached drawings upon which, by way of example, only the preferred embodiments of our invention are illustrated.

BRIEF DESCRIPTION OF THE DRAWINGS

FIG. 3 shows a cross-sectional view of the assembly of FIGS. 1–2 as viewed along cross-section lines 3—3 of FIG. 1 wherein a longitudinally movable catheter introducer needle and a similarly movable guide wire are shown in advanced operative positions.

FIG. 4 shows a cross-sectional view of the assembly of FIGS. 1–2, the same as viewed in FIG. 3, except that the needle and guide wire are shown in a retracted storage positions.

FIG. 7 shows a plan view of a catheter placement assembly employing a stationarily mounted wire as an obturator, thus illustrating another preferred embodiment of our invention.

FIG. 8 shows a side elevation view of the assembly of FIG. 7.

FIG. 9 shows a cross-sectional view of the assembly of FIGS. 7–8, as viewed from the same direction as in FIG. 8, and showing a longitudinally movable fenestrated needle in an advanced, operative position.

FIG. 10 shows a cross-sectional view of the assembly of FIGS. 7–9, the same as in FIG. 9 except that, in this view, the needle is shown in a retracted, storage position.

FIG. 11 shows a perspective view of a detachable body portion of the assembly of FIGS. 7–10, with the needle removed.

FIG. 12 shows a cross-sectional view of the body portion of FIG. 11 with the needle replaced and shown in a retracted, inoperative position.

DESCRIPTION OF THE PREFERRED EMBODIMENTS

Figures 1, 2:
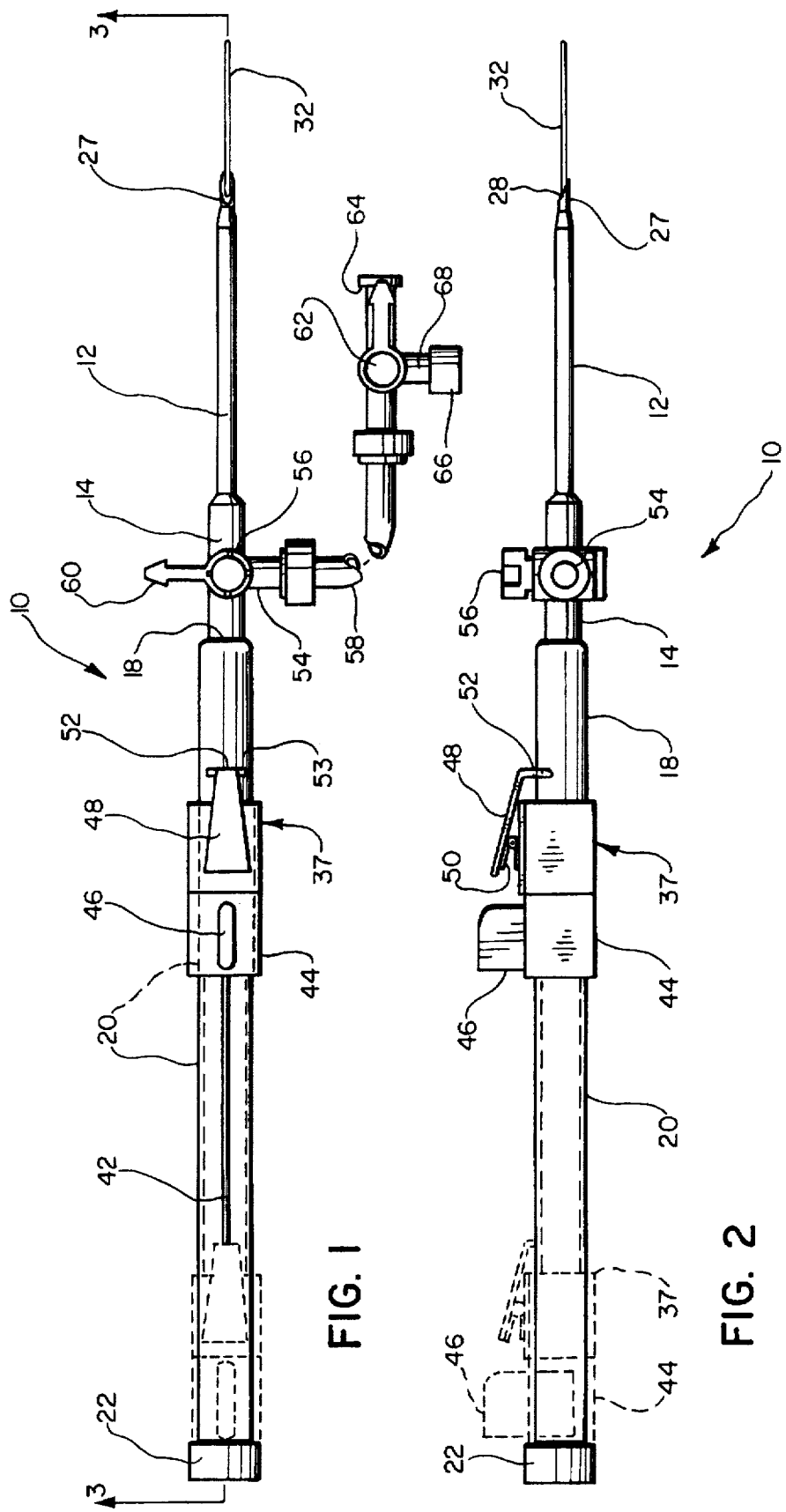
FIG. 1 shows a plan view of a catheter placement assembly, thus illustrating a preferred embodiment of our invention.
FIG. 2 shows a side elevation view of the assembly of FIG. 1.

Referring now to the drawing figures and, in particular, to FIGS. 1–6, there is shown, in one preferred embodiment of our invention, a catheter placement assembly generally designated 10. The assembly 10 includes two removably connected portions, a first of these being a flexible catheter 12 and hub 14 of the type through which a hypodermic needle, such as a catheter introducer needle, can be passed in close fitting relationship. While the catheter 12 and hub 14 can be removably connected together if desired, we prefer that they be permanently connected together in any suitable manner. A proximal end of the hub 14 is exteriorly threaded, as at 16, so as to threadably join an interiorly threaded open end portion of a thickened distal end portion 18 (See FIGS. 3–4) of the second of the aforementioned portions, namely, an elongate hollow sheath or tubular body 20 of uniform outside diameter throughout its length. An end cap 22 is friction fitted, glued or otherwise fastened to a proximal end of the tubular body 20. The thickened end portion 18 contains a needle guide passageway or a proximal end portion thereof which communicates with the open end portion.

The hub 14 contains a lumen 24 which extends between and opens onto distal and proximal ends thereof so as to communicate with a passageway 26 of the catheter 12 (See FIG. 4) and with an open distal end of the hollow body 20, respectively. Note that the hub lumen 24 is of relatively larger diameter than the catheter passageway 26 for reasons as later explained. An elongate, cannulated catheter introducer needle 27, having a sharp beveled tip 28 at its distal end and at least one, but, preferably, a plurality of spaced apart fenestrations 30 formed along a central portion of its length, is recessed entirely within the hollow interior 31 of the tubular body 20 when the needle 27 is in a fully retracted storage position as shown in FIG. 4. The tubular body 20 thus forms a needle attachment body to which the needle 27 is attached and provides a protective housing for the safe storage of the needle following its insertion into a liquid containing region, such as a blood vessel, of a biological organism such as a human or animal patient. Similarly, a flexible, longitudinally movable guide wire 32 is disposed entirely within the hollow interior 31 of the body 20 when in a fully retracted position as also shown in FIG. 4 and, in addition, is inserted through the cannula of the needle 27 when the latter is in its fully retracted position. The guide wire 32 is sufficiently longer than the needle 27 so as to be capable of extension forwardly beyond the tip 28 of the needle 27, when both the guide wire and needle are in their extended or advanced positions and after the needle is inserted into a blood vessel lumen, to provide a track over which to slide the catheter 12 when the latter is being inserted into the blood vessel lumen.

Figure 5:
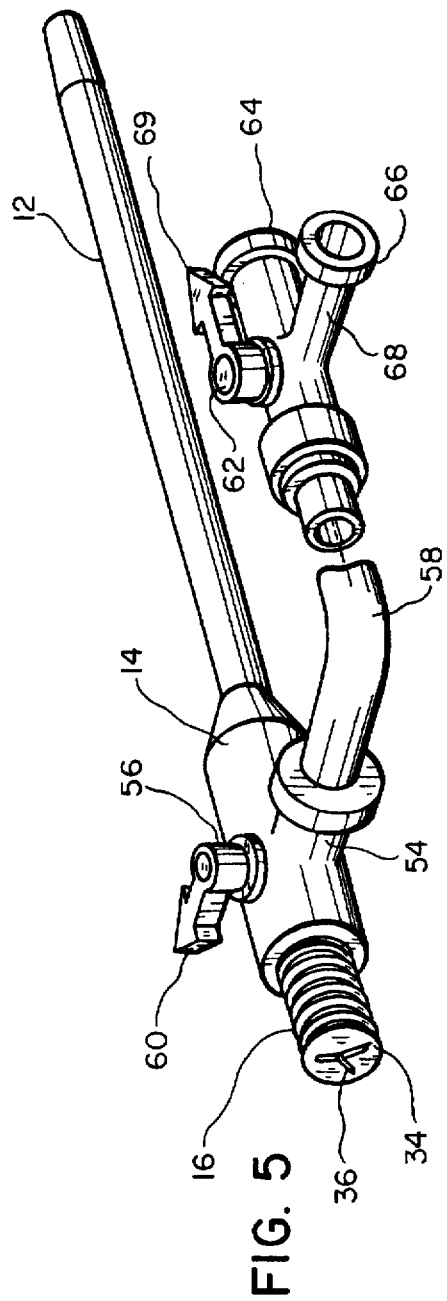
FIG. 5 shows a perspective view of a distal portion of the assembly of FIGS. 1–4.
Figure 6:
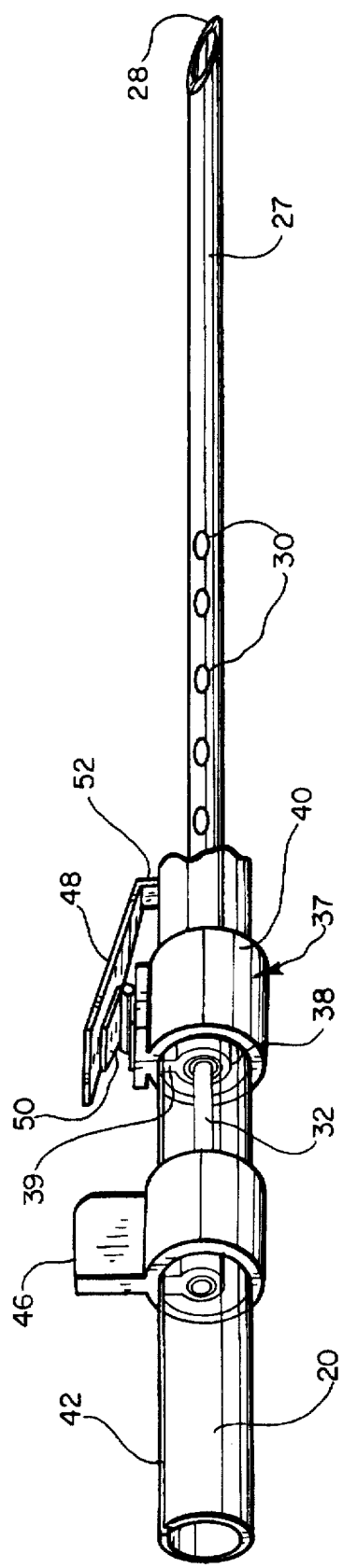
FIG. 6 shows a perspective view of another portion of the assembly of FIGS. 1–4.

A liquid sealing means, preferably in the form of a flexible, resilient diaphragm or septum 34, through which a hypodermic needle such as the needle 27 can be passed, and which may include a deformable slit, encloses the proximal end of the hub 14 in a liquid tight manner when in an unpenetrated condition insofar as the needle 27 is concerned as shown in FIGS. 4–5. The diaphragm 34 of the present example conventionally includes a three way slit 36 so that the guide wire 32 and, thereafter, the needle 27 will pass therethrough when moved from their retracted storage positions, as shown in FIG. 4, toward their advanced operative positions as shown in FIG. 3. The diaphragm 34 may be removably disposed in the hub 14 so as to seal an open proximal end of the threaded end portion 16 of the hub 14 so that it can be removed and replaced as needed. Also, the diaphragm 34 may be contained in a housing, which housing is preferably made of plastic and is removably attached to the hub 14 to seal the open proximal end of the hub 16, which accomplishes the same result. The purpose of the sealing means is to isolate the hollow interior of the body 20 from the lumen 24 of the hub 14 when the sealing means is in an unpenetrated condition. Presence of the guide wire 32 in the cannula of the needle 27 prevents blood or other body liquids from backing up into the hollow interior 31 of the tubular body 20 when the needle 27 is in its advanced operative position, as, for example, within a blood vessel. The guide wire 32 also prevents blood from passing through the needle 27 and the slit 36 into the body 20 from the hub lumen 24 as the needle 27 is being retracted through the lumen 24 after having made a blood vessel stick but before the tip 28 is withdrawn through the diaphragm 34.

A proximal end portion of the needle 27 is attached to a sleeve 37, which sleeve includes a first collar 38. The collar 38 is located within the hollow interior 31 of the body 20 and is attached by means of a radially extending wall 39 to a second collar 40 slidably surrounding the outer surface of the body 20. The body 20 defines a longitudinally extending slot 42 through which the wall 39 extends. Thus, the needle sleeve 37 can be moved longitudinally along the slot 42 in the body 20 to permit movement of the needle 27 between its fully retracted storage position and its fully extended operative position.

A similarly constructed sleeve 44 operates along the slot 42 and is connected to a proximal end of the guide wire 32.

The guide wire sleeve 44 is located behind the needle sleeve 37 so that, as the sleeve 37 and needle 27 are withdrawn toward the retracted position, the sleeve 44 and, hence, the guide wire 32 are also retracted. The guide wire sleeve 44 includes a radially projecting finger tab 46. The sleeve 37 also contains a stop element 48 which is spring biased, as at 50, to urge a tip 52 of the element 48 downwardly against the surface of the body 20 so as to insert into a circumferential slot 53 in the body 20 when the sleeve 37 is moved to the fully advanced position of the needle 27. The spring 50 may be a leaf spring or any other suitable type for the indicated purpose. In the alternative, the entire element 48 may be made of plastic and formed integral with the sleeve 37 (when also made of plastic) so that the tip 52 is naturally biased downwardly (as viewed) against the surface of the body 20 for insertion into the slot 53 when appropriately positioned.

The hub 14 also contains a liquid outlet port or side access port 54 which communicates with the hub lumen 24. A stop cock 56 is formed in the hub 14 to switch blood flow from the catheter 12 to either the port 54 or the hub end 16 as desired when the needle 27 is retracted from the hub 14. The stop cock 54 also has a portion which will permit blood to flow from the catheter 12 toward both the hub end 16 and the port 54 simultaneously and a position which will shut off flow from the catheter to both the hub end 16 and the port 54. A stop cock handle 60, when positioned as shown in FIGS. 1 and 5, permits blood flow from a blood vessel into the needle tip 28, thence through the needle 27 to the fenestration 30, thence through one or more of the fenestrations into the enlarged hub lumen 24 and, thereafter, through the port 54 into the line 58 when the guide wire 32 is at least partially retracted through the needle 27 rearwardly of the particular fenestration which communicates with the port 54. At this point, it should be noted that the diameter of the hub lumen must be somewhat greater than the outside diameter of the needle 27 so that blood or other body fluid introduced into the needle 27 can flow through one or more of the fenestrations 30 into the hub lumen 24 around the needle 27 when the needle 27 and the fenestrations 30 are properly positioned. When the handle 60 is rotated so as to point toward the port 54, the port 54 is sealed relative to the hub lumen 24 so that blood can not continue to flow through the port 54 into the line 58. The line 58 is connected to a second stop cock 62 which leads to an in-line outlet port 64. An air permeable, liquid impermeable membrane 66 is connected to a second outlet port 68 of the stop cock 62 such that, when a stop cock handle 69 is rotated to the position as shown in FIGS. 1 and 5, blood flow from the stop cock 56 through the line 58 will force air trapped in the line 58 and stop cock 62 downstream of the blood flow through the membrane 66 to ambient atmosphere. The port 64 may be connected to the transducer of a conventional blood pressure monitor to monitor the blood pressure of a patient with which the catheter 12 is used.

Preferably, the catheter hub 14 is formed of a rigid clear plastic so that a blood flash back can be readily observed therein upon successful penetration of the lumen of a blood vessel by the needle tip 28. The flexible line 58 can also be constructed of a transparent plastic so that blood flow can readily be observed therein, in which event the hub 14 need not necessarily be constructed of a clear plastic. However, we prefer and recommend that the hub 14 be constructed, at least in part, of a transparent or translucent material so that a blood flash back can be visually observed therein.

In actual operation, the assembly 10 is provided wherein, initially, the needle 27 and guide wire 32 are in the retracted stored conditions as shown in FIG. 4. Next, the needle sleeve 37 is slid forwardly along the tubular body 20 from its retracted position to its extended position as shown in FIG. 3 except that, for the time being, the guide wire sleeve 44, is left in its retracted condition as shown in FIG. 4. The tip 52 of the stop element 48 will catch in the slot 53 to hold the needle 27 in the desired advanced position. With the needle tip 28 just exposed beyond the distal end of the catheter 12 and with the guide wire 32 still fully retracted, the needle 27 is inserted into the body of a patient until the tip 28 penetrates the desired blood vessel lumen as indicated by blood flash back in the enlarged lumen 24 of the hub 14 and/or by blood flow into the line 58. Next, with the needle tip 28 penetrating the blood vessel lumen, the guide wire sleeve 44 is advanced along the body 20 until it is positioned against the needle sleeve 37 as shown in FIG. 3 wherein the guide wire 32 advances beyond the tip 28 of the needle 27 along the lumen of the blood vessel, assuming no substantial resistance to its advancement is encountered. If such resistance to the advancement of the guide wire 32 in the lumen of the blood vessel is encountered, the guide wire 32 can be retracted and the needle 27 repositioned while watching for blood flash back to confirm proper placement. Where attempts to reposition the needle 27 continue to be unsuccessful, the needle 27 and guide wire 32 can be removed from the blood vessel and body of the patient by sliding the needle sleeve 37 back to its retracted position and by choosing a new site on the patient for another needle stick. But, if there is no resistance to the advancement of the guide wire 32 along the blood vessel lumen, then, the second collar 40 is held between the thumb and middle finger of one hand while the stop element 48 is pressed with the index finger of the same hand to release the tip 52 from the slot 53. At the same time, the thumb and index finger of the other hand is used to grasp a distal end of the body 18 forward of the sleeve 37 and the body 18 is moved forwardly through the sleeve 37 until the catheter 12 is fully inserted into the skin of the patient. At this point, the body 18 ceases its forward movement but the first hand is used to move the sleeves 37 and 44 to their fully retracted positions. Next, with the needle 27 and guide wire 32 fully retracted as shown in FIG. 4 and with the catheter 12 inserted in the desired blood vessel, the body 20 is unscrewed from the hub 14 and safely disposed of according to standard safety procedures. Since the tip 28 of the needle 27 is well retracted within the open end of the body 20, the chance of incurring an accidental needle stick with the needle 27 is extremely remote if not altogether impossible. Access to the blood vessel is then available through the diaphragm 34, hub lumen 24 and port 54.

Referring now to FIGS. 7–12 there is shown, in another embodiment of our invention, a catheter placement assembly, generally designated 70, having a catheter 72 and a detachable sheath or hollow body portion 74. The catheter 72 includes a flexible cannulated catheter 76 having a passageway therethrough, and a hollow catheter hub 78 containing a lumen 79 which is substantially larger in diameter than that of the passageway through the catheter 72. As in the previous example, an optional three way stop cock 80 is formed in the hub 78. A flexible tube may be connected to an outlet port 82 of the hub 78 for transmitting blood from the hub 78 to a conventional blood pressure monitoring device, not shown, in the usual manner when the stop cock 80 is properly positioned. As in the previous example, the catheter hub 78, contains an exteriorly threaded proximal end portion 83 (FIGS. 9–10) which is threadably secured within an interiorly threaded distal end portion 87 of the body portion 74. A flexible, resilient diaphragm or septum 84, preferably containing a slit similar to the slit 36 in the diaphragm 34 of the previous example, forms a liquid sealing means which is affixed to the proximal end of the threaded end portion 83.

A longitudinally movable cannulated catheter introducer needle 85, containing one or more fenestrations 86, is recessed within the body portion 74 when the needle is in a retracted storage position as shown in FIGS. 10 and 12. The fenestrations 86 are positioned such that one or more of them communicate with the outlet port 82 when a handle 89 of the stop cock 80 is in the position as shown in FIG. 7 and when the needle 85 is in its advanced position as in FIGS. 7-9. All of the fenestrations are then disposed within the hub lumen distally of the diaphragm 34. A collar 88 surrounding the exterior surface of the body portion 74 can be moved by hand from a retracted position, shown in phantom at 88' in FIGS. 7-8, to an advanced position, as shown in full in those figures to move the needle 85 from its retracted position (FIG. 10) to its advanced operative position (FIGS. 7-9) along a longitudinally extending slit 90. The needle joining collar 88 of this example may be of the same construction as the needle joining collar 37 of the previous example.

Contrary to the previous example, the assembly 70 of the present example does not include a longitudinally movable guide wire. Rather, the assembly 70 includes an elongated, stationary obturator member, such as a wire 92, the proximal end of which is attached to an end cap 94. The wire 92 extends from the end cap 94 through the hollow body portion 74, through a thickened distal end portion 96 of the body portion 74 and into the interiorly threaded open end portion 87 (See FIGS. 11-12). When the catheter hub 78 is joined to the body portion 74, as shown in FIG. 10, a distal end portion of the wire 92 extends through the diaphragm 84. The wire 92 extends completely through the needle 85 when the latter is in its retracted storage position as shown best in FIGS. 10 and 12 and extends into a proximal end portion of the needle 85 and terminates proximal to the fenestrations 86 when the needle 85 is in its fully advanced, operative position. The wire 92 thus functions to force blood or other body fluids from the hollow interior of the needle 85, which may have accumulated therein when the needle 85 was in its advanced position, as the needle 85 is retracted along the wire 92 to its fully retracted position following insertion into a blood vessel. Any quantity of blood which is left in the needle 85 as the last of the fenestrations 86 is withdrawn from communication with the port 82 will be forced by the wire 92 either out of one or more of the fenestrations 86 or out of the distal end of the needle 85 into the hub 78 to the right of the diaphragm 84 as viewed in FIGS. 9-10 (distally) as the needle 85 is fully withdrawn through the diaphragm 84 into the body portion 74. The wire 92 also functions as a guide for the movement of the needle 85 in addition to keeping the body portion 74 free of blood. The body portion 74, in turn, functions as a secure needle containment unit when the needle 85 is disposed in its recessed and fully retracted position upon removal of the body portion 74 from the catheter hub 78 after use.

The side port 82, when connected to a clear plastic tube, permits blood to flow freely through the needle 85 and the fenestrations 86 into the tube to allow visual conformation of correct needle placement, including visual differentiation between steady venous blood flow and pulsating arterial blood flow. This can be accomplished without disconnecting the body portion 74 from the hub of the catheter portion 72 and without the spillage of blood.

In the present example of the invention, unlike the previous example, blood flow can be monitored continuously, even during initial advancement of the catheter into a blood vessel. The stop cock 80 permits use of the catheter hub 78 as an in line port for sampling blood and other body fluids when the body portion 74 is detached from the hub 78 and also permits use of the side port 82 for flexible placement of blood pressure monitoring and blood sample lines. The wire 92 can be made quite rigid if desired since it does not extend into a blood vessel for use as a guide wire and, therefore, does not need to be flexible.

Thus, a catheter assembly is provided for placement of a catheter with an introducer needle into a liquid containing region, such as a blood vessel, of a biological organism, which assembly contains a liquid sealing means in a catheter hub for substantially preventing a biological liquid introduced into the catheter from escaping the hub through the sealing means. A major source of viral and bacterial contamination is therefore greatly reduced, if not substantially eliminated, when using such an assembly. The needle can either be fixedly or movably attached to the assembly so long as it has an operative position for introducing the catheter into a biological subject. In addition, where a catheter introducer needle is movably attached to the assembly, a hollow sheath forming a needle attachment body is also provided wherein the needle can be safely housed following use to protect those handling the assembly from an accidental needle stick. Optionally, a side port is provided on a catheter hub to provide means for sampling a biological liquid introduced into the catheter, for monitoring blood pressure for sampling blood and for observing the flow of such a liquid in a line attached to the side port. A stop cock can be attached to the hub to direct liquid flow from the catheter to either the side port or in the direction of the sealing means or in both directions. A guide wire or an elongated obturator member can be employed to prevent the seepage of a liquid through the needle into the needle attachment body or sheath when the needle is in a position penetrating the sealing means. The needle is provided with one or more fenestrations to permit liquid flow from the needle cannula into the catheter hub for visual recognition of its presence and for pressure monitoring and access purposes.

Although the present invention has been described with respect to specific details of certain preferred embodiments thereof, it is not intended that such details limit the scope of our invention other than as specifically set forth in the following claims.

We claim:
1. A catheter assembly comprising
a flexible catheter defining a passageway,
a catheter hub having a distal end attached to a proximal end of said catheter, said hub defining a lumen which communicates on a distal end thereof with said passageway,
a flexible resilient diaphragm which can be penetrated by a hypodermic needle, such as a catheter introducer needle, said diaphragm being attached to said hub to seal a proximal end of said hub lumen in a liquid tight manner for preventing a liquid which has been introduced into said hub lumen from said catheter, external to a needle which may be penetrating said diaphragm and projecting into said hub lumen, from flowing through said diaphragm beyond said hub,
a needle attachment body connected to said hub, and
a cannulated catheter introducer needle having a sharp tip on a free end thereof and having an opposite end attached to said body such that said introducer needle has at least one position relative to said body which is operative to project through said diaphragm, hub lumen and catheter passageway when said body is attached to said hub for introducing said catheter into a liquid containing region of a biological organism, said introducer needle defining at least one fenestration on a central portion thereof which communicates with a cannula of said introducer needle and with said hub lumen and which is disposed within said hub lumen distally of said diaphragm when said introducer needle is disposed in said operative position.

2. The assembly of claim 1 wherein said hub is removably attached to one end of said catheter.

3. The assembly of claim 1 wherein said diaphragm defines a deformable slit.

4. The assembly of claim 1 wherein said diaphragm is removably attached to said hub.

5. The assembly of claim 1 wherein said hub is at least partially constructed of transparent material for permitting visual observation of a liquid flash back in said hub lumen upon the insertion of said catheter introducer needle through said hub, diaphragm and catheter into a positive pressure liquid containing region of a biological organism.

6. The assembly of claim 1 further comprising a liquid outlet port attached to a side of said hub, said liquid outlet port being in communication with said hub lumen distally of said diaphragm.

7. The assembly of claim 1 wherein said hub lumen is defined by at least one interior wall of said hub which is spaced apart from an outer surface of said introducer needle when said introducer needle is disposed in said operative position such that at least a portion of a liquid which has been introduced into said cannula can flow through said fenestration into said hub lumen, said hub being at least partially constructed of a material which permits visual observation of a presence of said liquid in said hub lumen.

8. The assembly of claim 1 wherein said introducer needle is movably attached to said body for longitudinal movement between a retracted storage position recessed within said body and said operative position.

9. The assembly of claim 1 further comprising a mechanism for moving said introducer needle longitudinally between a retracted storage position recessed within said needle attachment body and an operative position wherein said introducer needle extends beyond a distal end of said body, through said diaphragm, hub lumen and catheter passageway when said body is connected to said hub such that said tip is exposed beyond a distal end of said catheter.

10. The assembly of claim 1 wherein said needle attachment body comprises a hollow tubular sheath having an open distal end which is removably connected to a proximal end of said hub such that said open distal end and the hollow interior of said sheath are axially aligned with said hub lumen.

11. The assembly of claim 1 further comprising a device for occluding said needle cannula from a proximal end thereof and distally at least to and through said diaphragm, said occluding device thereby substantially preventing the flow of a liquid through said needle cannula and through said diaphragm into said needle attachment body.

12. The assembly of claim 1 wherein said introducer needle contains a plurality of fenestrations, all of which are in communication with said hub lumen distally of said diaphragm when said introducer needle is disposed in said operative position.

13. The assembly of claim 1 wherein said needle attachment body is removably connected to said hub.

14. The assembly of claim 1 wherein said hub is at least partially constructed of a translucent material for permitting visual observation of a liquid flash back in said hub lumen upon insertion of said catheter introducer needle through said hub, diaphragm and catheter into a positive pressure liquid containing region of a biological organism.

15. The assembly of claim 6 further comprising a stop cock attached to said hub and having a first position for directing the flow of a liquid from said catheter toward said diaphragm while blocking the flow of said liquid to said side outlet port, a second position for directing the flow of said liquid from said catheter toward said side outlet port while blocking the flow of said liquid toward said diaphragm, a third position for blocking the flow of said liquid from said catheter toward both said diaphragm and said side outlet port, and a fourth position for directing the flow of said liquid from said catheter toward both said diaphragm and said side outlet port.

16. The assembly of claim 9 wherein said needle moving mechanism comprises a sleeve including a first collar located in a hollow interior of said needle attachment body, said first collar being attached to a proximal end portion of said introducer needle, a second collar radially spaced from and surrounding said first collar, said second collar slidably surrounding an outer surface of said body, said body defining a longitudinally extending slit parallel to said introducer needle, and a wall joining said first collar to said second collar, said wall extending through said slit, whereby a sliding movement of said second collar along said body produces a corresponding longitudinal movement of said first collar along the hollow interior of said body to move said introducer needle.

17. The assembly of claim 11 wherein said occluding device comprises a flexible guide wire for guiding said catheter into a liquid containing region of a biological organism, said guide wire being longitudinally movable between a retracted position recessed within a hollow interior of said needle attachment body and an advanced position extending through said introducer needle and projecting beyond said tip when said introducer needle is disposed in said operative position.

18. The assembly of claim 11 wherein said occluding device comprises an elongated obturator member stationarily attached to said body and extending through said diaphragm into a proximal end portion of said hub lumen when said body is connected to said hub and into a proximal end portion of said introducer needle spaced proximally of said fenestration when said introducer needle is disposed in said operative position, for preventing a liquid contained in said introducer needle from flowing through said diaphragm into the hollow interior of said needle attachment body.

19. The assembly of claim 17 further comprising means for moving said guide wire including a first collar located in a hollow interior of said needle attachment body, said first collar being attached to a proximal end portion of said guide wire, a second collar radially spaced from and surrounding said first collar, said second collar slidably surrounding an outer surface of said body, said body defining a longitudinally extending slit parallel to said guide wire, and a wall joining said first collar to said second collar, said wall extending through said slit, whereby a sliding movement of said second collar along said body produces a corresponding longitudinal movement of said first collar along the hollow interior of said body to move said guide wire.

20. The assembly of claim 8 wherein said needle attachment body comprises an elongated hollow tube, said tube having a thickened distal end portion defining a cylindrically shaped needle passageway extending from a proximal end of said thickened end portion toward a distal end of said attachment body, a distal end portion of said tube having an open end portion communicating with said needle passageway and being adopted to attachably receive a proximal end portion of said hub therein in close fitting relationship, said diaphragm being attached to a proximal end of said hub for sealing a proximal end of said hub lumen in a liquid tight manner, said diaphragm being recessed within said open end portion when said tube is attached to said hub, the tip of said introducer needle being disposed in said needle passageway spaced proximally from said open end portion when said introducer needle is disposed in said retracted position.

21. The assembly of claim 20 wherein said open end portion of said tube is interiorly threaded and wherein the proximal end portion of said hub is exteriorly threaded such that said hub and said tube can be threadably joined.

22. A catheter assembly comprising a flexible catheter defining a passageway extending between open proximal and distal ends, a catheter hub having a distal end attached to a proximal end of said catheter, said hub defining a lumen which communicates with said passageway, a side access port communicating with said hub lumen, a needle attachment body connected to said hub, and a cannulated catheter introducer needle having a sharp tip on a free end thereof and having an opposite end attached to said body such that said introducer needle has at least one position relative to said body which is operative to project through said hub lumen and catheter passageway when said body is attached to said hub for introducing said catheter into a liquid containing region of a biological organism, said introducer needle defining at least one fenestration on a central portion thereof which communicates with a cannula of said introducer needle and, when said introducer needle is in said operative position, with said hub lumen and, a flexible resilient diaphragm attached between said body and a proximal end of said hub proximal to said side access port for preventing the flow of a liquid through said hub lumen past said side access port and through the proximal end of said hub external to said introducer needle cannula.

23. The assembly of claim 22 wherein said side access port is formed on said hub.

24. The assembly of claim 22 further comprising a multi-position stop cock operatively connected to said access port for selectively closing said access port in a liquid tight manner to prevent the flow of a liquid from said hub lumen through said access port.

25. The assembly of claim 22 wherein said hub is at least partially transparent.

26. The assembly of claim 22 wherein said hub is at least partially translucent.

27. The assembly of claim 22 wherein said at least one fenestration is disposed within said hub lumen when said introducer needle is disposed in said operative position.

28. The assembly of claim 22 wherein said needle attachment body is removably connected to said hub.

29. The assembly of claim 22 wherein said diaphragm is directly attached to said catheter hub.

30. The assembly of claim 23 further comprising a multi-position stop cock mounted on said hub and operatively projecting into said hub lumen for selectively isolating said access port from said hub lumen to prevent the flow of a liquid from said hub lumen through said access port.

31. A catheter assembly comprising a flexible catheter defining a passageway which extends between open proximal and distal ends, a catheter hub having a distal end attached to a proximal end of said catheter, said hub defining a lumen which extends between open proximal and distal ends and which communicates on a distal end thereof with said passageway, a flexible, resilient diaphragm which can be penetrated by a hypodermic needle, such as a catheter introducer needle, said diaphragm being attached to said hub to seal a proximal end of said hub lumen in a liquid tight manner for preventing a liquid which has been introduced into said hub lumen from said catheter, external to a needle which may be penetrating said diaphragm and projecting into said hub lumen, from flowing through said diaphragm beyond said hub, a needle attachment body removably connected to said hub, and a cannulated catheter introducer needle having a sharp tip on a free end thereof and having an opposite end attached to said body such that said introducer needle has at least one position relative to said body which is operative to project through said diaphragm, hub lumen and catheter passageway when said body is attached to said hub for introducing said catheter into a liquid containing region of a biological organism, said introducer needle defining at least one fenestration on a central portion thereof which communicates with a cannula of said introducer needle and with said hub lumen and which is positioned distally of said diaphragm when said introducer needle is disposed in said operative position.

32. A catheter assembly comprising a flexible catheter defining a passageway extending between open proximal and distal ends, a catheter hub having a distal end attached to a proximal end of said catheter, said hub defining a lumen therethrough which communicates with said passageway, a hollow needle attachment body connected to said hub, a cannulated catheter introducer needle having a sharp tip on a free end thereof and being movably attached to said body and reciprocally movable longitudinally between a retracted storage position recessed within said body and an operative position projecting out of said body through said hub lumen and catheter passageway for introducing said catheter into a liquid containing region of a biological organism, said needle defining at least one fenestration on a central portion thereof which communicates with a cannula of said needle and, when said needle is disposed in said operative position, with said hub lumen.

33. The assembly of claim 32 wherein said fenestration is located within said hub lumen when said needle is disposed in said operative position.

34. The assembly 32 further comprising a flexible resilient diaphragm which can be penetrated by a needle, such as a catheter introducer needle, said diaphragm being attached to said hub for preventing a liquid which has been introduced into said hub lumen from flowing external to said introducer needle through said diaphragm and beyond said hub, said fenestration being located distally of said diaphragm when said introducer needle is disposed in said operative position.

35. The assembly of claim 32 wherein said needle attachment body is removably connected to said hub.

36. The assembly of claim 32 further comprising an occluding device for blocking at least a proximal end portion of said introducer needle to prevent a liquid which has been introduced into a cannula of said introducer needle from flowing through said introducer needle beyond a proximal end of said hub.

37. The assembly of claim 34 wherein said fenestration is located in said hub lumen when said introducer needle is disposed in said operative position.

38. A catheter assembly comprising a flexible catheter defining a passageway therethrough, a hub having a distal end attached to a proximal end of said catheter, said hub defining a lumen therethrough which communicates with said passageway, a hollow needle attachment body connected to said hub, and a cannulated catheter introducer needle having a sharp tip on a free end thereof and being movably attached to said body and reciprocally movable longitudinally between a retracted storage position recessed within said body and an operative position projecting out of said body through said hub lumen and catheter passageway for introducing said catheter into a liquid containing region of a biological organism, and an elongated movable guide member for providing a guide for advancing said catheter into a biological organism, said guide member being attached to said attachment body and aligned for movement through a cannula of said needle.

39. The assembly of claim 38 wherein said guide member is sized to occlude at least a proximal end portion of said cannula to prevent a liquid which has been introduced into said needle from flowing into said needle attachment body.

* * * * *

UNITED STATES PATENT AND TRADEMARK OFFICE
CERTIFICATE OF CORRECTION

PATENT NO. : 5,704,914
DATED : Jan. 6, 1998
INVENTOR(S) : John E. Stocking, et al It is certified that error appears in the above-indentified patent and that said Letters Patent is hereby corrected as shown below:

Col. 1, line 30,
       "robe" should read --tube--

Signed and Sealed this

Twenty-fourth Day of February, 1998

Attest:

BRUCE LEHMAN

Attesting Officer      *Commissioner of Patents and Trademarks*